(12) United States Patent
Tokuda et al.

(10) Patent No.: US 6,710,204 B2
(45) Date of Patent: Mar. 23, 2004

(54) DECREASING METHOD OF N-OXYL COMPOUND

(75) Inventors: Masanori Tokuda, Otake (JP); Yasukazu Yoshida, Ikeda (JP); Junichi Doi, Otake (JP); Motomu Oh-Kita, Tokyo (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 122 days.

(21) Appl. No.: 10/103,867

(22) Filed: Mar. 25, 2002

(65) Prior Publication Data

US 2003/0078425 A1 Apr. 24, 2003

(30) Foreign Application Priority Data

| Mar. 26, 2001 | (JP) | 2001-087805 |
|---|---|---|
| Mar. 26, 2001 | (JP) | 2001-087806 |
| May 30, 2001 | (JP) | 2001-162453 |

(51) Int. Cl.[7] .......................... C08C 67/48; C08L 5/057
(52) U.S. Cl. ...................... 560/248; 524/174; 210/633; 560/234
(58) Field of Search ...................... 524/174; 210/633; 560/234, 248

(56) References Cited

U.S. PATENT DOCUMENTS

| 5,554,785 A | * 9/1996 | Trapasso et al. ............ 560/201 |
|---|---|---|
| 5,760,265 A | 6/1998 | Takahara et al. |

FOREIGN PATENT DOCUMENTS

| JP | 50-145449 | 11/1975 |
|---|---|---|
| JP | 1-258642 | 10/1989 |
| JP | 4-66555 | 3/1992 |
| JP | 8-259498 | 10/1996 |
| JP | 10-36319 | 2/1998 |
| JP | 11-222462 | 8/1999 |

* cited by examiner

*Primary Examiner*—Samuel A. Acquah
(74) *Attorney, Agent, or Firm*—Oblon, Spivak, McClelland, Maier & Neustadt, P.C.

(57) ABSTRACT

There is provided a superior decreasing method of an N-oxyl compound contained in an easily polymerizable material, according to which the N-oxyl compound contained in an easily polymerizable material can be sufficiently decreased and loss of the easily polymerizable material is little. The easily polymerizable material containing an N-oxyl compound and an acid are contacted with each other. In addition, not only the N-oxyl compound but also an organic titanium group compound contained in the easily polymerizable material can be sufficiently decreased.

12 Claims, No Drawings

DECREASING METHOD OF N-OXYL COMPOUND

FIELD OF THE INVENTION

The present invention relates to a decreasing method of an N-oxyl compound contained in an easily polymerizable material. More specifically, the present invention relates to a decreasing method of an N-oxyl compound contained in (meth)acrylic acid or a (meth)acrylic acid ester. Further, the present invention relates to a decreasing method of an organic titanium group compound further contained in the easily polymerizable material.

BACKGROUND OF THE INVENTION

With respect to an improving method of characteristics of an ester plasticizer, JP-A-50-145449 discloses a process for producing an ester plasticizer, which comprises the step of allowing an alcohol having a specific carbon atom number to react with an aromatic acid or an aliphatic acid having a specific carbon atom in the presence of a catalyst, thereby obtaining an ester, and the step of contacting the obtained ester with a combination of an activated clay and at least one of a magnesium oxide and a calcium oxide in the presence of water. In the literature, it is disclosed that according to said process, impurities such as unreacted acids, monoesters, the catalyst and by-products, which cause to deteriorate characteristics of the plasticizer, are removed, and as a result, the characteristics can be improved. In the literature, it is further disclosed that a titanium compound such as a tetraalkyl titanate is enumerated as the catalyst used for the production of such an ester. Further, in the literature, there is disclosed a process comprising the step of adding an activated clay, at least one of MgO and CaO and water to the obtained ester at the same time, or adding an activated clay thereto, followed by successive addition of at least one of MgO and CaO and water, and the step of filtering the resulting mixture. It is also disclosed that a water content is suitably from 0.1 to 1% by weight based on the weight of the ester.

JP-A-10-36319 discloses a process for producing an ester, which comprises the step of contacting an ester obtained by reaction between an alcohol and an acid with a compound having both a solid acid and a solid base in the molecule. In the literature, it is disclosed that in producing the ester, the ester, namely a final product is desired to be small in a metal ion content, colorless and low in its acid value, and for that purpose, the ester obtained by reaction between an alcohol and an acid in the presence of an acid catalyst or a metal compound catalyst is treated with an adsorbent, thereby removing various impurities such as impurities contained in the raw materials for the production, by-products produced at the time of production and purification and catalyst residues, and an active carbon, an activated clay and the like can be used as the adsorbent. Further, in the literature, it is disclosed that in the case where an activated clay is used in a manner as proposed in JP-B-59-38254 (corresponding to JP-A-50-145449), there has been left a problem such that physical adsorption and electrostatic adsorption mainly proceed, so that a cation exchange is caused between the activated clay and the metal ion remained in the ester, thereby discharging a proton, and as a result, an acid value of the ester increases to deteriorate a stability.

JP-A-11-222462 discloses a process for producing a high purity (meth)acrylic acid ester, according to which in producing the (meth)acrylic acid ester by the reaction between methyl (meth)acrylate and an alcohol having a specific carbon atom number, tetramethyl titanate and a specific N-oxyl compound are used as a catalyst and a polymerization inhibitor, respectively.

While, JP-A-1-258642 discloses a process comprising the step of using a titanium alkoxide and a steric hindrance phenol as the catalyst and the polymerization inhibitor, respectively, in carrying out a transesterification between a carboxylic acid ester and an alcohol and a direct esterification between a carboxylic acid and an alcohol. Further, JP-A-4-66555 discloses a process comprising the step of using a titanium alkoxide as the catalyst, whose alkoxide is derived from the same alcohol as that used as the material.

Furthermore, with respect to a separating method of such a titanium alkoxide from a reaction product by a means other than distillation, JP-A-8-259498 (corresponding to U.S. Pat. No. 5,760,265) discloses a process, according to which a titanium group metal carboxylate used in the direct esterification between a carboxylic acid and an alcohol is made soluble in water with use of a chelating agent, and then extracted.

SUMMARY OF THE INVENTION

An easily polymerizable material such as various monomers used as materials for producing a polymer can be usually obtained from a petroleum material. Such an easily polymerizable material polymerizes itself due to heat or light or the like, and therefore a polymerization inhibitor is usually added during a production or purification process. The polymerization inhibitor is usually contained also to the easily polymerizable material itself after the production thereof. There are known many compounds to be added to monomers as the polymerization inhibitor. Of these, an N-oxyl compound has a superior polymerization inhibiting ability.

However, when a lot of the polymerization inhibitor is contained in the monomer, a lot of a polymerization initiator is needed when carrying out the polymerization to produce a polymer. A problem of such a polymerization obstruction is remarkable particularly when the monomer contains an N-oxyl compound having a high polymerization inhibiting ability.

As a decreasing method of the polymerization inhibitor contained in the monomer before polymerization, there is known a process for separating the polymerization inhibitor from the monomer by means of distillation. However, according thereto, there is left a problem such that a loss of the monomer is large, a recovery rate is low, and moreover the N-oxyl compound cannot be sufficiently separated or decreased. Further, there is a possibility of polymerization because the monomer is necessarily heated.

As a catalyst used for a transesterification between a carboxylic acid ester and alcohols and a direct esterification between a carboxylic acid and alcohols, there are known a metal catalyst such as an organic titanium group compound and an organic tin based catalyst; an acid catalyst such as p-toluene sulfonic acid, sulfuric acid and a strongly acidic ion exchange resin; and a base catalyst such as a solid base and a strongly basic ion exchange resin.

Of these, an organic titanium group compound, whose typical example is a titanium alkoxide, is extremely high in reaction activity and selectivity, and therefore of extensively wide use as a catalyst in the transesterification and direct esterification.

However, since the catalyst of the organic titanium group compound per se generally dissolves in a reaction liquid, it is necessary to separate the catalyst from the reaction product.

With respect to the separation operation of the catalyst, it is general to carry out the separation by distillation. However, the distillation inevitably causes a loss of a product (a desired product), requires a lot of energy and time and greatly increases costs for apparatus or the like. Moreover, there is a possibility of polymerization during distillation, in the case where the desired product is an unsaturated carboxylic acid ester.

Still, according to the method other than distillation as disclosed in the above-mentioned JP-A-8-259498, there is left a problem such that a lot of waste water is produced, thereby placing a severe load on the environment.

The present invention has been accomplished in the light of these problems. It is an object of the present invention to provide a superior decreasing method of an N-oxyl compound, according to which the N-oxyl compound contained in an easily polymerizable material can be sufficiently decreased with a little loss of the easily polymerizable material.

It is another object of the present invention to economically and industrially and easily remove not only an organic titanium group compound catalyst but also an organic titanium group compound derived from said catalyst from an easily polymerizable material such as an unsaturated carboxylic acid ester, which material has been obtained by a reaction using an organic titanium group compound catalyst, for example, a transesterification reaction between a vinyl group-containing unsaturated carboxylic acid ester and an alcohol or a direct esterification reaction between a vinyl group-containing unsaturated carboxylic acid and an alcohol.

That is, the present invention provides a decreasing method of an N-oxyl compound, which comprises the step of bringing an easily polymerizable material containing an N-oxyl compound into contact with an acid. The present invention also provides a decreasing method of not only the N-oxyl compound but also an organic titanium group compound catalyst, when the easily polymerizable material further contains an organic titanium group compound catalyst.

These methods in accordance with the present invention are suitable when the N-oxyl compound is at least one component selected from the group consisting of N-oxyl compounds represented by the following formulas (1) to (3),

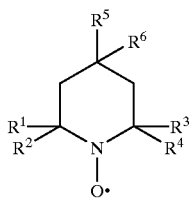

(1)

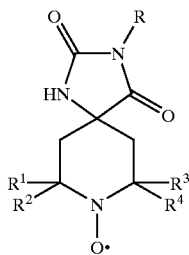

(2)

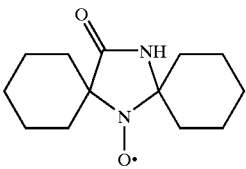

(3)

wherein $R^1$, $R^2$, $R^3$ and $R^4$ are each an alkyl group having 1 to 8 carbon atoms, the alkyl can be a straight chain or branched one, or at least one of a combination of $R^1$ and $R^2$ and a combination of $R^3$ and $R^4$ can be united to form a ring; $R^5$ is H, OH, OR, OCOR, NHCOR or $O\text{-}[(EO)_n\text{+}(PO)_m]\text{-}H$; and $R^6$ is H; or $R^5$ and $R^6$ together can represent =O; in which R is a hydrogen atom or an alkyl, alkenyl or aryl group having 1 to 18 carbon atoms, in which the alkyl can be a straight chain or branched one and the aryl can be one whose hydrogen atom is substituted with an alkyl group, EO represents an ethyleneoxy group, PO represents a propyleneoxy group; and n and m can be the same as or different from each other and are each an integer of 0 to 10, provided that n and m are not 0 at the same time.

DETAILED DESCRIPTION OF THE INVENTION

In the present invention, the easily polymerizable material includes a polymerizable compound such as a vinyl group-containing unsaturated carboxylic acid and a vinyl group-containing unsaturated carboxylic acid ester. Examples of the unsaturated carboxylic acid include acrylic acid and methacrylic acid. Examples of the unsaturated carboxylic acid ester include methyl acrylate, ethyl acrylate, butyl acrylate, 2-ethylhexyl acrylate, methyl methacrylate, ethyl methacrylate, butyl methacrylate, 2-ethylhexyl methacrylate and lauryl methacrylate. The present invention is suitably applied, when the easily polymerizable material is (meth) acrylic acid or a (meth)acrylic ester.

The N-oxyl compound includes a compound containing a nitroxyl radical, which is formed by binding an oxygen radical to a nitrogen atom. For example, compounds represented by the above formulas (1) to (3) are enumerated. Specific examples of the N-oxyl compound represented by the formula (1) include 2,2,6,6-tetramethylpiperidine-N-oxyl, 4-hydroxy-2,2,6,6-tetramethylpiperidine-N-oxyl (compound 1), 4-acetamino-2,2,6,6-tetramethylpiperidine-N-oxyl (compound 8), 4-acetyloxy-2,2,6,6-tetramethylpiperidine-N-oxyl, 4-acryloyloxy-2,2,6,6-tetramethylpiperidine-N-oxyl (compound 4), 4-methacryloyloxy-2,2,6,6-tetramethylpiperidine-N-oxyl (compound 5), 4-benzoyloxy-2,2,6,6-tetramethylpiperidine-N-oxyl (compound 6), 4-methoxy-2,2,6,6-tetramethylpiperidine-N-oxyl, 4-ethoxy-2,2,6,6-tetramethylpiperidine-N-oxyl, 4-phenoxy-2,2,6,6-tetramethylpiperidine-N-oxyl (compound 2), 4-benzyloxy-2,2,6,6-tetramethylpiperidine-N-oxyl (compound 3), 4-acryloylamino-2,2,6,6-tetramethylpiperidine-N-oxyl (compound 9), 4-methacryloylamino-2,2,6,6-tetramethylpiperidine-N-oxyl (compound 10), 4-benzoylamino-2,2,6,6-tetramethylpiperidine-N-oxyl (compound 11), 4-cinnamoylamino-2,2,6,6-tetramethylpiperidine-N-oxyl (compound 12), 4-crotonylamino-2,2,6,6-tetramethylpiperidine-N-oxyl, 4-propionylamino-2,2,6,6-tetramethylpiperidine-N-oxyl, 4-butylylamino-2,2,6,6-tetramethylpiperidine-N-oxyl, 2,2, 6,6-tetramethyl-4-piperidone-N-oxyl, 4-[H-(EO)$_2$-O]-2,2,6, 6-tetramethylpiperidine-N-oxyl (compound 13), 4-[H-(EO)$_4$-O]-2,2,6,6-tetramethylpiperidine-N-oxyl (compound 18), 4-[H-(EO)$_6$-O]-2,2,6,6-tetramethylpiperidine-N-oxyl (compound 20), 4-[H-(EO)$_8$-O]-2,2,6,6-tetramethylpiperidine-N-oxyl (compound 23), 4-[H-(EO)$_{10}$-O]-2,2,6,6-tetramethylpiperidine-N-oxyl (compound 26), 4-[H-[(EO)$_2$+(PO)$_4$]-O]-2,2,6,6-tetramethylpiperidine-N-oxyl, 4-[H-[(EO)$_4$+(PO)$_3$]-O]-2,2,6,6-tetramethylpiperidine-N-oxyl, 4-[H-[(EO)$_6$+(PO)$_3$]-O]-2,2,6,6-tetramethylpiperidine-N-oxyl (compound 21), 4-[H-(PO)$_{10}$-O]-2,2,6,6-tetramethylpiperidine-N-oxyl (compound 31), 4-[H-(PO)$_6$-O]-2,2,6,6-tetramethylpiperidine-N-oxyl (compound 30) and 4-[H-[(EO)$_5$+(PO)$_{10}$]-O]-2,2,6,6-tetramethylpiperidine-N-oxyl. Table 1 and Table 2 summarize typical examples of these compounds and other N-oxyl compounds.

TABLE 1

| N-Oxyl compounds | wherein $R^1$, $R^2$, $R^3$ and $R^4$ are each a methyl group, $R^6$ is H, and $R^5$ is a group as shown below. |
|---|---|
| 1 | OH |
| 2 | O-φ |
| 3 | OCH$_2$φ |
| 4 | OCOCH=CH$_2$ |
| 5 | OCOC(CH$_3$)=CH$_2$ |
| 6 | OCOφ |
| 7 | OCOCH=CH-φ |
| 8 | NHCOCH$_3$ |
| 9 | NHCOCH=CH$_2$ |
| 10 | NHCOC(CH$_3$)=CH$_2$ |
| 11 | NHCOφ |
| 12 | NHCOCH=CH-φ |

(Note: φ is a phenyl group.)

TABLE 2

| N-Oxyl compounds | wherein $R^1$, $R^2$, $R^3$ and $R^4$ are each a methyl group, $R^6$ is H, $R^5$ is O—[(EO)$_n$ + (PO)$_m$]—H, in which n and m are each an integer as shown below. | |
|---|---|---|
| | n | m |
| 13 | 2 | 0 |
| 14 | 2 | 1 |
| 15 | 2 | 2 |
| 16 | 3 | 0 |
| 17 | 3 | 3 |
| 18 | 4 | 0 |
| 19 | 4 | 4 |
| 20 | 6 | 0 |
| 21 | 6 | 3 |
| 22 | 6 | 6 |
| 23 | 8 | 0 |

TABLE 2-continued

| 24 | 8 | 4 |
| 25 | 8 | 8 |
| 26 | 10 | 0 |
| 27 | 10 | 5 |
| 28 | 10 | 9 |
| 29 | 0 | 3 |
| 30 | 0 | 6 |
| 31 | 0 | 10 |

As the N-oxyl compound represented by the formula (2), the following compound A and compound B are enumerated.

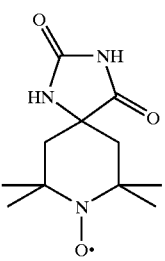

(A)

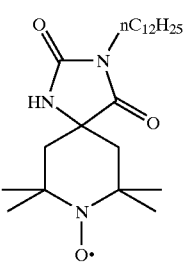

(B)

Furthermore, cyclohexane-1-spiro-2'-(4'-oxoimidazolidine-1'-oxyl)-5'-spiro-1"-cyclohexane represented by the formula (3) can be used.

One kind or more than one kind of the N-oxyl compound may be contained in the easily polymerizable material. The present invention can be also applied even when polymerization inhibitors other than the N-oxyl compound such as hydroquinone, hydroquinone monomethyl ether and phenothiazine are contained in the easily polymerizable material. The present invention can be preferably applied to the easily polymerizable material containing the N-oxyl compounds represented by the formulas (1) to (3). An amount of the N-oxyl compound contained in the easily polymerizable material is not particularly limited. In many cases, the N-oxyl compound as the polymerization inhibitor is added in an amount of from 0.01 to 5000 ppm based on the weight of the easily polymerizable material.

In the easily polymerizable material containing an N-oxyl compound, for example, an organic titanium group compound or the like may be contained. One example of easily polymerizable materials, which contain the organic titanium group compound in addition to the N-oxyl compound, includes a desired product-containing reaction liquid, which can be obtained by transesterification between a carboxylic acid ester, namely the easily polymerizable material, and an alcohol, or direct esterification between a carboxylic acid, namely the easily polymerizable material, and an alcohol, wherein the reactions are carried out in the presence of an N-oxyl compound and a catalyst of a titanium group metal alkoxide. The other example thereof is the desired product, which is separated from the above-mentioned reaction liquid and in which the N-oxyl compound and the organic titanium group compound are contained. Incidentally, the organic titanium group compound means a compound containing the Group IV elements (Ti, Zr, Hf) in the periodic table of elements.

As the carboxylic acid ester used in the above instance as the easily polymerizable material, for example, acrylic acid esters and methacrylic acid esters are enumerated. Particularly, (meth)acrylic acid esters such as methyl acrylate, ethyl acrylate, butyl acrylate, methyl methacrylate, ethyl methacrylate and butyl methacrylate are preferably used. As used herein, the term "(meth)acryl" refers to "acryl" or "methacryl", or both "acryl" and "methacryl" as conventionally used.

As the alcohol allowed to react with the carboxylic acid ester in the transesterification and the alcohol allowed to react with the carboxylic acid in the direct esterification reaction, there are enumerated, for example, alkanols, alkoxyalkanols, alkenoxyalkanols, alkenols, phenols, phenoxyalkanols, cycloalkanols, alkylcycloalkanols, cycloalkylalkanols, phenylalkanols, alkylphenylalkanols, haloalkanols, cyanoalkanols and aminoalkanols. Of these, more preferred are alkanols, alkenols and aminoalkenols, and particularly preferred are alkanols.

Preferred are alcohols having 3 to 20 carbon atoms, and specific examples thereof are n-propanol, isopropanol, n-butanol, isobutanol, tertiary butanol, n-pentanol, n-hexanol, n-heptanol, n-octanol, 2-ethyl-hexanol, lauryl alcohol, tridecyl alcohol, stearyl alcohol, tridecanol, dimethylamino ethanol, diethylamino ethanol, cyclohexanol, 3,3,5-trimethylcyclohexanol, 4-tertiary-butylcyclohexanol, phenol, benzyl alcohol, 1-phenylethyl alcohol, 2-phenylethyl alcohol, phenoxyethanol, methoxyethanol, ethoxyethanol, butoxyethanol, allyl alcohol and methallyl alcohol.

In the transesterification and the direct esterification, a feeding ratio between the carboxylic acid ester or the carboxylic acid and the alcohol is not particularly limited. From a viewpoint of productivity of the desired carboxylic acid ester, the starting carboxylic acid ester or the carboxylic acid is used in an amount of preferably from 0.1 to 10.0 moles, more preferably from 0.3 to 4.0 moles, per mole of the alcohol.

As the organic titanium group compound catalyst used in the transesterification and the direct esterification, there are exemplified those having a formula, M $R^1 R^2 R^3 R^4$, wherein M is Ti, Zr or Hf; $R^1$, $R^2$, $R^3$ and $R^4$ are halogen, OH, OR, OCOR or NHCOR; or $R^1$ and $R^2$ may be united to form =O; in which R is a hydrogen atom or an alkyl, alkenyl or aryl group having 1 to 18 carbon atoms, wherein the alkyl may be a straight chain or branched one substituted or unsubstituted with halogen, cyano or alkylamino, and the aryl may be one whose hydrogen atom is substituted with an alkyl group. Specific examples thereof are tetramethoxytitanium, tetraethoxytitanium, tetra-i-propoxytitanium, tetrabutoxytitanium including tetra-n-butoxytitanium, tetra(2-ethylhexyloxy)titanium, tetrastearyloxytitanium, di-i-propoxybis(acetylacetonato) titanium, di-n-butoxybis(triethanolaminato)titanium, tri-n-butoxytitanium stearate, isopropoxytitanium tristearate, tetramethoxyzirconium, tetraethoxyzirconium, tetra-i-propoxyzirconium, tetrabutoxyzirconium including tetra-n-butoxyzirconium, tetra(2-ethylhexyloxy)zirconium, tetrastearyloxyzirconium, tetramethoxyhafnium, tetraethoxyhafnium, tetra-i-propoxyhafnium, tetrabutoxy-hafnium including tetra-n-butoxyhafnium, tetra(2-ethylhexyloxy) hafnium and tetrastearyloxyhafnium.

The organic titanium group compound catalyst is used in an amount of preferably from 0.00001 to 0.1 mole, more preferably from 0.0001 to 0.05 mole, and much more preferably from 0.0003 to 0.03 mole, per mole of the starting alcohol.

It is assumed that the organic titanium group compound catalyst may partially or wholly vary to an organic titanium group compound different from the starting catalyst after completion of the transesterification and the direct esterification. How to vary is not clear. In the case where the starting catalyst is M $R^1 R^2 R^3 R^4$, it is assumed that the resulting compound contains an organic titanium group compound, in which $R^1$, $R^2$, $R^3$ and $R^4$ are partially or wholly changed to the starting alcohol or a hydroxyl or ester group. In the present specification, such an organic titanium group compound caused by change of the starting catalyst is referred to as "organic titanium group compound derived from the catalyst".

The transesterification between the carboxylic acid ester and the alcohol and the direct esterification between the carboxylic acid and the alcohol can be carried out in a conventional manner. Reaction conditions are not particularly limited. That is, a reaction pressure may be any of reduced pressure, atmospheric pressure or increased pressure, and a reaction temperature can be appropriately determined. From a viewpoint of polymerization inhibition, it is recommendable to make the reaction temperature not higher than 150° C.

In the transesterification and direct esterification, an alcohol or water is produced as a by-product as the reaction proceeds. Such a by-product can be taken out of the reaction system in the form an azeotropic mixture with the carboxylic acid ester or a suitable solvent. Completion of the reaction can be confirmed in a manner such that no azeotropic mixture distills out or one of the materials in the reaction system is completely consumed.

The present invention is characterized by bringing the easily polymerizable material containing an N-oxyl compound into contact with an acid. The acid used in the present invention is not particularly limited in its kind. Examples thereof are aqueous solutions of inorganic acids such as sulfuric acid, hydrochloric acid, nitric acid and phosphoric acid; aqueous solutions of organic acids such as sulfonic acid compounds; and solid acids such as an acidic ion exchange resin including a strongly acidic ion exchange resin and an activated clay. Of these, preferred are solid acids, which are easy to deal with. More preferred are an activated clay and a strongly acidic ion exchange resin, which are high in efficiency of removing the N-oxyl compound. Particularly preferred are an activated clay.

As the acid used for decreasing the N-oxyl compound from the easily polymerizable material containing both the N-oxyl compound and the organic titanium group compound, preferred are solid acids such as strongly acidic ion exchange resins and activated clays, because such solid acids are capable of decreasing the organic titanium group compound as well as the N-oxyl compound.

These solid acids have moisture absorption ability. The moisture absorption ability is closely related to the removal of the organic titanium group compound. A moisture content of the solid acids is preferably not less than 0.1% by weight, and particularly preferably not less than 2% by weight. In general, there is a tendency such that the moisture content of the solid acids increases with increase of the removal ability of the organic titanium group compound.

How to contact the easily polymerizable material containing an N-oxyl compound and the acid with each other is not particularly limited. When a liquid such as an inorganic or organic acid aqueous solution is used as the acid, it is permitted to use a process comprising the step of contacting an aqueous layer of the acid aqueous solution and a layer of the easily polymerizable material containing an N-oxyl compound with each other by means of stirring or the like. In the case where two layers are contacted with each other in such a manner, the easily polymerizable material can be isolated by extraction.

While, when the solid acid is used as the acid, it is permitted to use a process comprising the step of contacting the easily polymerizable material and the acid with each other for a specific period of time in a continuous or batch manner using, for example, a fluidized vessel, a fixed bed or the like. When the process other than that using a fixed bed is used, the solid acid can be taken out by means of solid-liquid separation operation such as filtration and decantation, thereby isolating the easily polymerizable material. Conditions including an amount of the acid to be used, a contacting time of the easily polymerizable material with the acid and so on are not particularly limited, and can be determined depending upon amounts of the N-oxyl compound and the organic titanium group compound contained in the easily polymerizable material and degrees of the N-oxyl compound and organic titanium group compound to be decreased. For example, the solid acid is used in an amount of preferably from 1 to 200 parts by weight, more preferably from 10 to 100 parts by weight, per part by weight of the organic titanium group compound catalyst. There is a tendency such that with increasing said amount, more sufficient removal of the N-oxyl compound and the organic titanium group compound can be attained, and with decreasing the amount, loss of the desired product can be decreased. When the contact is carried out, for example, in a batch manner, a time of contacting the acid used with the easily polymerizable material is preferably from 1 to 120 minutes. As long as the contacting time is within said range, there is a tendency such that with shortening the time, production of impurities due to a side reaction can be decreased, and with prolonging the time, the organic titanium group compound can be sufficiently removed. A contacting temperature is not particularly limited. Preferred is from 0 to 200° C., more preferred is from ambient temperature to 200° C., and much more preferred is from 40 to 120° C.

EXAMPLES

The present invention is explained with reference to Examples and Comparative Examples as follows. The N-oxyl compounds used were expressed by the compound number as shown in Table 1 and Table 2. Methyl methacrylate of an easily polymerizable material is abbreviated to MMA. A content of the N-oxyl compound in a monomer was determined according to a high performance liquid chromatography. A content of a titanium group metal was determined according to an ICP spectrometry. As used herein, the conversion is as follows.

Conversion(%)=(mole number of the starting alcohol consumed by reaction)/(mole number of the starting alcohol fed)×100

Example 1

In a 300 ml four necked flask, 100 g of MMA containing 100 ppm of the N-oxyl compound 8 and 0.5 g of an activated clay, GALEONEARTH GSF (manufactured by Mizusawa Chemical Industries Ltd.) were fed, and the mixture was stirred for 60 minutes at ambient temperature. After completion of the stirring, the resulting liquid was filtered using a membrane filter having a pore diameter of 0.5 μm, thereby obtaining 98.7 g of MMA (recovery 98.7%). A content of the N-oxyl compound 8 contained in the resulting MMA was found to be not more than a minimum limit of determination (0.1 ppm).

Example 2

Decreasing treatment of the N-oxyl compound was carried out in the same manner as in Example 1, except that 100 g of MMA containing 20 ppm of the N-oxyl compound 1 as a polymerization inhibitor was used, thereby obtaining 98 g of MMA (recovery 98%). A content of the N-oxyl compound 1 contained therein was found to be not more than a minimum limit of determination (0.1 ppm).

Example 3

Decreasing treatment of the N-oxyl compound was carried out in the same manner as in Example 1, except that 100 g of ethylene glycol dimethacrylate was used in place of said MMA, thereby obtaining 98.5 g of ethylene glycol dimethacrylate (recovery 98.5%). A content of the N-oxyl compound 8 contained therein was found to be not more than a minimum limit of determination (0.1 ppm).

Example 4

Decreasing treatment of the N-oxyl compound was carried out in the same manner as in Example 1, except that 100 g of lauryl methacrylate was used in place of said MMA, thereby obtaining 98.3 g of lauryl methacrylate (recovery 98.3%). A content of the N-oxyl compound 8 contained therein was found to be not more than a minimum limit of determination (0.1 ppm).

Example 5

Decreasing treatment of the N-oxyl compound was carried out in the same manner as in Example 1, except that 10 g of a strongly acidic ion exchange resin, Amberlist 15 (manufactured by Rohm and Haas Ltd.) was used in place of said activated clay, thereby obtaining 97.7 g of MMA (recovery 97.7%). A content of the N-oxyl compound 8 contained therein was found to be not more than a minimum limit of determination (0.1 ppm).

Example 6

In a 300 ml four necked flask, 100 g of MMA containing 50 ppm of the N-oxyl compound 8 and 100 g of 10% sulfuric acid aqueous solution were fed, and the mixture was stirred for 60 minutes at ambient temperature. After completion of the stirring, the aqueous layer was separated using a separating funnel, thereby obtaining 96.9 g of MMA (recovery 96.9%). A content of the N-oxyl compound 8 contained in the resulting MMA was found to be not more than a minimum limit of determination (0.1 ppm).

Comparative Example 1

In a 500 ml four necked flask equipped with a 10 stage Oldershaw type distilling column, 300 g of MMA containing 20 ppm of the N-oxyl compound 8 was fed, the flask was immersed in an oil bath of 80° C., and distillation was continued under reduced pressure of 10 kPa until MMA was no longer distilled out, thereby obtaining 280 g of MMA (recovery 93.3%). A content of the N-oxyl compound 8 was found to be 1.2 ppm. Thus, it was demonstrated that the N-oxyl compound could not be sufficiently decreased according to such a method.

Comparative Example 2

In a 500 ml four necked flask equipped with a 10 stage Oldershaw type distilling column, 300 g of lauryl methacrylate containing 20 ppm of the N-oxyl compound 8 was fed, the flask was immersed in an oil bath of 180° C., and distillation was continued under reduced pressure of 0.1 kPa until lauryl methacrylate was no longer distilled out, thereby obtaining 238 g of lauryl methacrylate (recovery 79.3%). A content of the N-oxyl compound 8 was found to be 18 ppm. Thus, it was demonstrated that the N-oxyl compound could not be sufficiently decreased according to such a method.

Example 7

Using a refluxing apparatus equipped with a 20 stage Oldershaw type distilling column, in a 2 l-volume four necked flask equipped with a side tube were fed 902 g (9 moles) of MMA, 389 g (5.2 moles) of n-butyl alcohol, 0.89 g of tetrabutoxytitanium and 0.05 g of the N-oxyl compound 8, and the mixture was stirred under air atmosphere for 2.5 hours to complete transesterification. As a result of analysis of the reaction liquid by gas chromatography, the conversion was found to be 99.9%. During the transesterification, methanol produced as a by-product of the reaction was taken out of the system in a form of an azeotropic mixture with MMA. Then, a temperature of the reaction liquid rose from 104° C. to 130° C.

Successively, 22 g (25 parts by weight per part by weight of a catalyst) of an activated clay (SA1 manufactured by Japan Activated Clay, Ltd., a moisture content being 10% by weight) was added to the reaction liquid, and the mixture was stirred at 50° C. for 60 minutes. The treated liquid was filtered using a membrane filter having a pore diameter of 0.5 μm. Thereafter, unreacted MMA and n-butanol were distilled out under reduced pressure, thereby obtaining 722 g of purified n-butyl methacrylate (yield 96.8%). A content of the N-oxyl compound 8 contained in the resulting purified n-butyl methacrylate was found to be not more than a minimum limit of determination (0.1 ppm), and titanium was also found to be not more than a minimum limit of determination (30 ppb). Incidentally, a period of time from completion of the transesterification to production of the purified n-butyl methacrylate was found to be 4 hours.

Comparative Example 3

Example 7 was repeated to obtain a purified n-butyl methacrylate, except that the treatment using the activated clay was replaced by a purification treatment by distillation. In the purification treatment by distillation, unreacted MMA and butanol were distilled out under reduced pressure, and thereafter distillation was carried out at 120° C. under pressure of 13.3 kPa.

Thereby, 672 g (yield 90.1%) of purified n-butyl methacrylate was obtained. A content of the N-oxyl compound 8 contained in the purified n-butyl methacrylate was found to be 1.0 ppm, and that of titanium was found to be not more than a minimum limit of determination (30 ppb). The yield of n-butyl methacrylate was lower than that in Example 7, and a period of time from completion of the transesterification to production of the purified n-butyl methacrylate was found to be 6 hours.

Examples 8 to 13

Example 7 was repeated, provided that reactions and treatments of the catalyst were carried out under conditions as shown in Table 3. In every Examples, a period of time from completion of the transesterification to production of the purified carboxylic acid ester was found to be 4 hours, a content of the N-oxyl compound 8 contained in the obtained purified carboxylic acid ester was found to be not more than a minimum limit of determination (0.1 ppm), and that of the metal titanium group was also found to be not more than a minimum limit of determination (30 ppb).

TABLE 3

| | Upper stand: starting carboxylic acid ester<br>Middle stand: starting alcohol<br>Lower stand: produced carboxylic acid ester | Catalyst | Reaction temperature (° C.) | Upper stand: solid acid<br>Middle stand: water content<br>Lower stand: amount used (per part by weight of a catalyst) |
|---|---|---|---|---|
| Example 8 | MMA<br>n-butanol<br>n-butyl methacrylate | tetrabutoxytitanium | 101–130 | strongly acidic ion exchange resin<br>10 wt %<br>81 parts by weight |
| Example 9 | MMA<br>lauryl alcohol<br>lauryl methacrylate | tetramethoxytitanium | 101–120 | activated clay<br>10 wt %<br>62 parts by weight |
| Example 10 | methyl acrylate<br>isobutanol<br>iso-butyl acrylate | tetramethoxytitanium | 84–115 | activated clay<br>10 wt %<br>22 parts by weight |
| Example 11 | ethyl acetate<br>n-butanol<br>butyl acetate | tetrabutoxytitanium | 84–93 | activated clay<br>10 wt %<br>24 parts by weight |
| Example 12 | MMA<br>n-butanol<br>n-butyl methacrylate | tetrabutoxyzirconium | 100–129 | activated clay<br>10 wt %<br>21 parts by weight |
| Example 13 | MMA<br>n-butanol<br>n-butyl methacrylate | tetrabutoxyhafnium | 100–129 | activated clay<br>10 wt %<br>21 parts by weight |

Example 14

Using a refluxing apparatus equipped with a 20 stage Oldershaw type distilling column, in a 2 l-volume four necked flask equipped with a side tube were fed 750.9 g (7.5 moles) of MMA, 676.3 g (2.5 moles) of stearyl alcohol, 1.23 g of tetramethoxytitanium and 0.04 g of the N-oxyl compound 8, and the mixture was stirred under air blowing for 4 hours to complete transesterification. As a result of analysis of the reaction liquid by gas chromatography, the conversion was found to be 100%. During the transesterification, methanol produced as a by-product of the reaction was taken out of the system in a form of an azeotropic mixture with MMA. Then, a temperature of the reaction liquid rose from 110° C. to 121° C.

Successively, 39 g (32 parts by weight per part by weight of a catalyst) of an activated clay (SA1 manufactured by Japan Activated Clay, Ltd., a moisture content being 2% by weight) was added to the reaction liquid, and the mixture was stirred at 50° C. for 60 minutes. The treated liquid was filtered using a membrane filter having a pore diameter of 0.5 μm. Thereafter, unreacted MMA was distilled out under reduced pressure, thereby obtaining 827.5 g of purified stearyl methacrylate (yield 97.8%). A content of the N-oxyl compound 8 contained in the resulting purified stearyl methacrylate was found to be not more than a minimum limit of determination (0.1 ppm), and titanium was also found to be not more than a minimum limit of determination (30 ppb). Incidentally, a period of time from completion of the transesterification to production of the purified stearyl methacrylate was found to be 4 hours.

Example 15

Example 14 was repeated, except that 19.5 g (16 parts by weight per part by weight of a catalyst) of an activated clay (SA1 manufactured by Japan Activated Clay, Ltd., a moisture content being 10% by weight) was used as a solid acid, thereby obtaining 830.1 g of purified stearyl metharylate (yield 98.1%). A content of the N-oxyl compound 8 contained in the resulting purified stearyl methacrylate was found to be not more than a minimum limit of determination (0.1 ppm), and titanium was found to be not more than a minimum limit of determination (30 ppb).

Example 16

Example 14 was repeated, except that 6.5 g (5.3 parts by weight per part by weight of a catalyst) of an activated clay (SA1 manufactured by Japan Activated Clay, Ltd., a moisture content being 30% by weight) was used as a solid acid, thereby obtaining 838.8 g of purified stearyl metharylate (yield 99.1%). A content of the N-oxyl compound 8 contained in the resulting purified stearyl methacrylate was found to be not more than a minimum limit of determination (0.1 ppm), and titanium was found to be not more than a minimum limit of determination (30 ppb).

Example 17

Example 14 was repeated, except that 19.5 g (16 parts by weight per part by weight of a catalyst) of an activated clay (SA1 manufactured by Japan Activated Clay, Ltd., a moisture content being 2% by weight) was used as a solid acid, thereby obtaining 833.4 g of purified stearyl metharylate (yield 98.5%). A content of the N-oxyl compound 8 contained in the resulting purified stearyl methacrylate was found to be not more than a minimum limit of determination (0.1 ppm), and titanium was found to be 7 ppm.

EFFECTS OF THE INVENTION

According to the present invention, the N-oxyl compound contained in the easily polymerizable material can be sufficiently decreased with a little loss of the easily polymerizable material. The present invention is particularly effective, when the N-oxyl compound contained in the easily polymerizable material is at least one of N-oxyl compounds represented by the formulas (1) to (3).

In the present invention, loss of the easily polymerizable material can be further lowered by using a solid acid, particularly an activated clay as the acid.

The present invention is suitably applied when the easily polymerizable material is (meth)acrylic acid or a (meth) acrylic acid ester.

According to the present invention, in producing an unsaturated carboxylic acid ester using an organic titanium group compound as a catalyst, the organic titanium group compound and an organic titanium group compound derived from the catalyst can be removed from the unsaturated carboxylic acid ester obtained by the reaction economically and industrially easily.

What is claimed is:

1. A decreasing method of an N-oxyl compound, which comprises the step of bringing an easily polymerizable material containing an N-oxyl compound into contact with an acid.

2. The decreasing method of an N-oxyl compound according to claim 1, wherein the N-oxyl compound is at least one component selected from the group consisting of N-oxyl compounds represented by the following formulas (1) to (3),

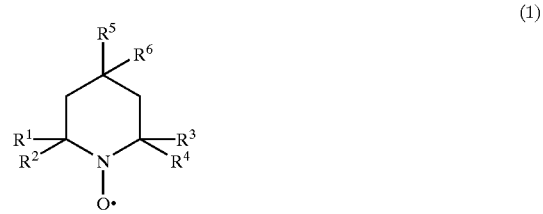

(1)

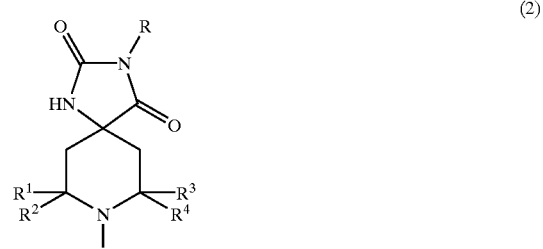

(2)

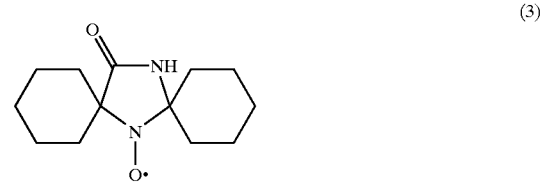

(3)

wherein $R^1$, $R^2$, $R^3$ and $R^4$ are each an alkyl group having 1 to 8 carbon atoms, in which the alkyl can be a straight chain or branched one, or at least one of a combination of $R^1$ and $R^2$ and a combination of $R^3$ and $R^4$ can be united to form a ring; $R^5$ is H, OH, OR, OCOR, NHCOR or O-[(EO)$_n$+ (PO)$_m$]-H; and $R^6$ is H; or $R^5$ and $R^6$ together can represent =O; in which R is a hydrogen atom or an alkyl, alkenyl or aryl group having 1 to 18 carbon atoms, in which the alkyl can be a straight chain or branched one and the aryl can be one whose hydrogen atom is substituted with an alkyl group, EO represents an ethyleneoxy group, PO represents a propyleneoxy group; and n and m can be the same as or different from each other and are each an integer of 0 to 10, provided that n and m are not 0 at the same time.

3. The decreasing method of an N-oxyl compound according to claim 1, wherein the acid includes a solid acid.

4. The decreasing method of an N-oxyl compound according to claim 2, wherein the acid includes a solid acid.

5. The decreasing method of an N-oxyl compound according to claim 3, wherein the solid acid includes at least one component selected from the group consisting of an activated clay and a strongly acidic ion exchange resin.

6. The decreasing method of an N-oxyl compound according to claim 4, wherein the solid acid includes at least one component selected from the group consisting of an activated clay and a strongly acidic ion exchange resin.

7. The decreasing method of an N-oxyl compound according to claim 3, wherein the solid acid includes an activated clay.

8. The decreasing method of an N-oxyl compound according to claim 4, wherein the solid acid includes an activated clay.

9. The decreasing method of an N-oxyl compound according to claims 1 to 8, wherein the easily polymerizable material includes (meth)acrylic acid or a (meth)acrylic acid ester.

10. The decreasing method of an N-oxyl compound according to claims 1 to 8, wherein the easily polymerizable material containing an N-oxyl compound further contains an organic titanium group compound.

11. The decreasing method of an N-oxyl compound according to claim 10, wherein the organic titanium group compound includes a titanium group metal alkoxide.

12. The decreasing method of an N-oxyl compound according to claim 10, wherein the easily polymerizable material containing an N-oxyl compound used includes a reaction liquid containing a product which is obtained by conducting a transesterification between a carboxylic acid ester, which is the easily polymerizable material, and an alcohol, in the presence of an N-oxyl compound and a titanium group metal alkoxide catalyst.

* * * * *